US00PP18734P2

(12) United States Plant Patent
Zaiger et al.

(10) Patent No.: US PP18,734 P2
(45) Date of Patent: Apr. 15, 2008

(54) NECTARINE TREE NAMED 'ROYAL RUBY'

(50) Latin Name: ***Prunus persica* var. *nucipersica***
Varietal Denomination: Royal Ruby

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 0 days.

(21) Appl. No.: 11/601,962

(22) Filed: Nov. 21, 2006

(51) Int. Cl.
*A01H 5/00* (2006.01)

(52) U.S. Cl. ..... Plt./190
(58) Field of Classification Search ..... Plt./190
See application file for complete search history.

*Primary Examiner*—Kent Bell
*Assistant Examiner*—June Hwu

(57) ABSTRACT

A new and distinct variety of nectarine tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. The tree having a low winter chilling requirement of approximately 300 hours at or below 45° F.
2. Fruit with firm flesh, good handling and shipping quality.
3. Vigorous, upright tree growth.
4. Fruit ripening in the early maturity season.
5. Fruit with good flavor and eating quality.
6. Heavy and regular production of fruit.

1 Drawing Sheet

Botanical classification: *Prunus persica* var. *nucipersica.*

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries and interspecifics are exemplary. It was against this background of our activities that the present variety of nectarine tree was originated and asexually reproduced by us in our experimental orchard located near Modesto, Stanislaus County, Calif.

PRIOR VARIETIES

Among the existing varieties of nectarine and peach trees, which are known to us, and mentioned herein, 'Red Roy' Nectarine (U.S. Plant Pat. No. 12,057), 'May Grand' Nectarine (U.S. Plant Pat. No. 2,794), 'Royal Gold' Peach (U.S. Plant Pat. No. 2,663), 'May Glo' Nectarine (U.S. Plant Pat. No. 5,245), 'Ruby Gold' Nectarine (U.S. Plant Pat. No. 3,101) and 'Sun Red' Nectarine (non-patented).

ORIGIN OF THE VARIETY

The new and distinct variety of nectarine tree (*Prunus persica* var. *nucipersica*) was developed by us in our experimental orchard located near Modesto, Calif. as a first generation cross between 'Red roy' Nectarine (U.S. Plant Pat. No. 12,057) and the proprietary nectarine '57Z707'. The paternal parent originated as a second generation proprietary parent from crosses between 'May Grand' Nectarine (U.S. Plant Pat. No. 2,794), 'Royal Gold' Peach (U.S. Plant Pat. No. 2,663), 'May Glo' Nectarine (U.S. Plant Pat. No. 5,245), 'Ruby Gold' Nectarine (U.S. Plant Pat. No. 3,101), 'Sun Red' Nectarine (non-patented) and two proprietary nectarine selections '3W8' and '2W68W'. A large number of these first generation seedlings were grown and budded to older trees of 'Nemaguard' Rootstock (non-patented), to accelerate rapid fruit production for evaluation. Under close and careful observation we recognized the desirable fruit characteristics of one seedling, which is the present nectarine variety and selected it in 2000 for additional asexual propagation and commercialization.

ASEXUAL REPRODUCTION OF THE VARIETY

Asexual reproduction of the new and distinct variety of nectarine tree was by budding to 'Nemaguard' Rootstock (non-patented), as performed by us in our experimental orchard located near Modesto, Calif. and shows that reproductions run true to the original tree and all characteristics of the tree and its fruit are established and transmitted through succeeding asexual propagations.

SUMMARY OF THE NEW VARIETY

The new variety of nectarine tree is of large size, vigorous, upright growth and a productive and regular bearer of large, yellow flesh, clingstone fruit with good flavor and eating quality. The fruit is further characterized by ripening in the early maturity season, having an attractive red skin color, firm flesh with good handling and shipping quality, being nearly globose in shape and relatively uniform in size throughout the tree. The tree having a relatively low winter chilling requirement of approximately 300 hours at or below 45° F. In comparison to its maternal parent 'Red Roy' Nectarine (U.S. Plant Pat. No. 12,057), the tree of the new variety requires approximately 50 hours less winter chilling and the fruit of the new variety is approximately 18 days earlier in maturity. In comparison to the paternal parent '57Z707', the tree of the new variety fruit matures 6 days later, the fruit is larger in size, and fruit set is more consistent from year to year.

PHOTOGRAPH OF THE VARIETY

The accompanying color photographic illustration shows typical specimens of the foliage and fruit of the present new nectarine variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of nectarine tree, 6 years of age, its flowers, foliage and fruit, as based on observations of 6 year old specimens grown near Modesto, Calif., with color in accordance with Munsell Book of Color.

Tree:

*Size.*—Large, normal for most nectarine varieties. Usually pruned to 3 to 3.5 meters in height for economical harvesting of fruit. Average spread 3 meters, varies with different cultural practices.

*Vigor.*—Vigorous, growth of 1½ to 2 meters in height the first growing season, varies with type of soil, fertility and climatic conditions.

*Form.*—Upright, usually pruned to vase shape.

*Branching habit.*—Upright, crotch angle approximately 30°, increases with heavy crop load.

*Productivity.*—Productive, fruit thinning and spacing necessary for desired market size. Number of fruit set varies with climatic conditions at bloom time.

*Bearer.*—Regular, adequate fruit set 4 consecutive years, no alternate bearing observed.

*Fertility.*—Self-fertile.

*Density.*—Medium dense, pruning to vase shape increases sunlight and air movement to center of tree to enhance fruit color and health of fruit wood.

*Hardiness.*—Tree grown in USDA Hardiness Zone 9. Hardy in all stone fruit growing areas of California. Winter chilling requirement approximately 300 hours at or below 45° F.

Trunk:

*Size.*—Large. Average circumference 47.2 cm at 20.3 cm above ground on a 6 year old tree.

*Stocky.*—Medium stocky.

*Texture.*—Medium shaggy, increases with age.

*Color.*—Varies from 10YR 3/4 to 2.5Y 5/2.

Branches:

*Size.*—Medium size. Average circumference 20.5 cm at 1.2 meters above ground.

*Surface texture.*—New growth relatively smooth. Mature growth varies from medium rough to rough, increases with age.

*Lenticels.*—Size — large. Average number 41 in a 25.8 sq cm area. Average length 4.4 mm. Average width 1.5 mm. Color varies from 10YR 7/8 to 10YR 6/8.

*Color.*—New growth varies from 2.5GY 5/8 to 2.5GY 5/6. Old growth varies from 10YR 3/4 to 10YR 3/6. Varies with age of growth.

Leaves:

*Size.*—Medium to large. Average length 127.3 mm. Average width 40.4 mm.

*Form.*—Lanceolate.

*Apex.*—Acuminate.

*Base.*—Cuneate.

*Margin.*—Crenate.

*Thickness.*—Medium.

*Surface texture.*—Upper surface relatively smooth, slightly indented over midrib and leaf veins, glabrous. Lower surface relatively smooth with small ridges created by midrib and pinnate venation, glabrous.

*Petiole.*—Size — medium. Average length 10.4 mm. Average width 1.5 mm. Grooved longitudinally. Surface — glabrous. Color varies from 5GY 5/6 to 5GY 4/6.

*Glands.*—Type — reniform. Size — medium to large. Average length 1.7 mm. Average diameter 0.8 mm. Number — average 2, varies from 1 to 3. Located primarily on base of leaf blade and upper portion of petiole. Color varies from 2.5GY 6/6 to 2.5GY 5/6.

*Color.*—Upper surface varies from 5GY 3/6 to 7.5GY 3/6. Lower surface varies from 5GY 5/4 to 5GY 4/6. Midvein color varies from 2.5GY 7/8 to 2.5GY 6.6.

Flower buds:

*Size.*—Medium. Average length 16.7 mm. Average width 10.2 mm.

*Hardiness.*—Hardy in all stone fruit growing areas of California. Grown in USDA Hardiness Zone 9.

*Form.*—Conical, becoming elongated before opening.

*Pedicel.*—Average length 5.6 mm. Average width 0.9 mm. Color varies from 5GY 6/6 to 5GY 5/6.

*Color.*—Varies from 5RP 7/10 to 7.5RP 7/8.

Flowers:

*Size.*—Large, showy. Average height 19.7 mm. Average diameter 34.1 mm.

*Petals.*—Number — 5, alternately arranged to sepals. Average length 17.8 mm. Average width 17.2 mm. Form — obovate. Margin — sinuate. Color varies from 5RP 8/4 to 5RP 7/6, fades with age of flower. Both surfaces glabrous.

*Sepals.*—Number — 5, alternately arranged to petals. Shape — ovate, apex rounded. Average length 7.1 mm. Average width 5.9 mm. Margin — entire. Upper surface glabrous, lower surface pubescent. Color — upper surface varies from 10Y 6/6 to 2.5GY 5/4. Lower surface varies from 5RP 2/4 to 7.5RP 3/4.

*Stamens.*—Average number per flower 43. Average filament length 13.8 mm. Filament color N 9.5/(white) to 5RP 8/4. Anther color 5Y 8.5/8 to 5Y 8/8.

*Pollen.*—Self fertile. Color varies from 5Y 8/8 to 5Y 7/10.

*Pistil.*—Number — normally one. Surface — glabrous. Average length 21.4 mm. Position of stigma — average of 3.6 mm above anthers. Color varies from 10Y 8/6 to 2.5GY 7/6.

*Fragrance.*—Slight aroma.

*Blooming period.*—Date of First Bloom Feb. 1, 2005. Date of Petal Fall Feb. 11, 2005, varies slightly with climatic conditions.

*Color.*—Varies from 7.5RP 8/4 to 5RP 8/4.

*Number flowers per flower bud.*—One.

*Pedicel.*—Average length 5.3 mm. Average width 1.2 mm. Color varies from 5GY 5/6 to 5GY 7/8.

Fruit:

*Maturity when described.*—Firm ripe.

*Date of first picking.*—May 10, 2005.

*Date of last picking.*—May 16, 2005, varies slightly with climatic conditions.

*Size.*—Large. Average diameter axially 59.5 mm. Average transversely in suture plane 63.2 mm. Average weight 133.5 grams, varies slightly with fertility of the soil, amount of thinning and climatic conditions.

*Form.*—Globose.

*Suture.*—Nearly smooth, extends from base to apex.

*Ventral surface.*—Very slightly lipped.

*Apex.*—Varies from slight tip to slightly retuse.

*Base.*—Retuse.

*Cavity.*—Rounded to slightly elongated in suture plane. Average length 5.1 mm. Average diameter 11.9 mm.

Stem:

*Size.*—Small to medium. Average length 7.9 mm. Average diameter 3.0 mm.

*Color.*—Varies from 5GY 5/8 to 5GY 4/8.

Flesh:

*Ripens.*—Relatively even, very slightly earlier near apex.

*Texture.*—Firm, meaty.

*Fibers.*—Few, small, tender.

*Firmness.*—Good, comparable to 'Red Roy' Nectarine (U.S. Plant Pat. No. 12,057).

*Aroma.*—Very slight.

*Amydgalin.*—Undetected.

*Eating quality.*—Good.

*Flavor.*—Good.

*Juice.*—Moderate, enhances flavor.

*Brix.*—Average 8.9°, varies slightly with amount of fruit per tree and climatic conditions.

*Color.*—Varies from 5Y 8/10 to 5Y 7/12. Pit cavity varies from 2.5Y 7/10 to 5Y 7/12.

Skin:

*Thickness.*—Medium.

*Surface.*—Relatively smooth.

*Down.*—Wanting.

*Tendency to crack.*—None.

*Color.*—Ground color varies from 5Y 8/6 to 7.5Y 8/8. Overspread with 5R 2/8 to 7.5R 3/10.

*Tenacity.*—Tenacious to flesh.

*Astringency.*—None.

Stone:

*Type.*—Clingstone.

*Size.*—Large. Average length 32.5 mm. Average width 27.0 mm. Average thickness 20.6 mm.

*Form.*—Ovoid.

*Base.*—Varies from flat to rounded.

*Apex.*—Slightly pointed. Average length 0.7 mm.

*Surface.*—Pitted throughout, pits vary from round to elongated.

*Sides.*—Unequal, with one side extending further from suture plane.

*Ridges.*—Relatively smooth, wide, extending from base toward apex.

*Tendency to split.*—None.

*Color.*—Varies from 2.5Y 8/6 to 10YR 5/8.

Kernal:

*Form.*—Ovate.

*Taste.*—Bitter.

*Viability.*—Poor, embryo only partially developed.

*Size.*—Medium. Average length 16.9 mm. Average width 14.3 mm. Average depth 5.9 mm.

*Skin.*—Color varies from 2.5Y 8.5/4 to 10YR 5/6.

Use: Dessert. Market — local and long distance.

Keeping quality: Good, held firm in cold storage at 38° to 42° for 2 weeks without internal breakdown or appreciable loss of flavor.

Shipping quality: Good, minimal skin scarring or bruising of flesh during picking and packing trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of nectarine tree, its flowers, foliage and fruit herein described may vary in slight detail due to climate, soil conditions and cultural practices under which the variety may be grown. The present description is that of the variety grown under the ecological conditions prevailing near Modesto, Calif.

It is claimed:

1. A new and distinct variety of nectarine tree (*Prunus persica* var. *nucipersica*), substantially as illustrated and described, characterized by its large size, vigorous, upright growth, a low winter chilling requirement of approximately 300 hours at or below 45° F., being a productive and regular bearer of large, yellow, flesh, clingstone fruit with good flavor and eating quality; the fruit is further characterized by having firm flesh with an attractive red skin color and good handling and shipping quality.

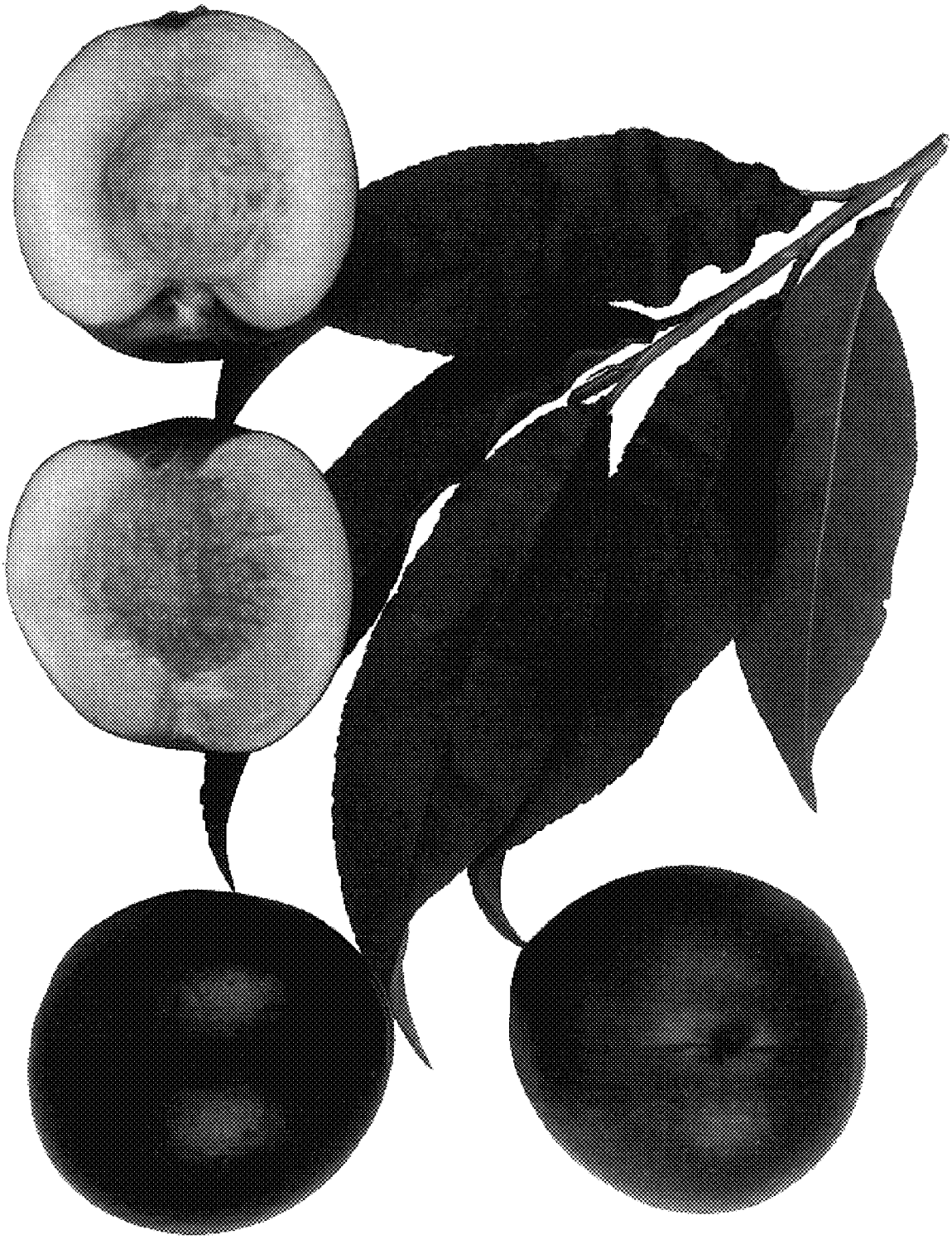

* * * * *